(12) United States Patent
Hirokawa et al.

(10) Patent No.: US 11,954,872 B2
(45) Date of Patent: Apr. 9, 2024

(54) IMAGE PROCESSING METHOD, PROGRAM, AND IMAGE PROCESSING DEVICE

(71) Applicant: NIKON CORPORATION, Tokyo (JP)

(72) Inventors: Mariko Hirokawa, Yokohama (JP); Yasushi Tanabe, Fujisawa (JP)

(73) Assignee: NIKON CORPORATION, Tokyo (JP)

( * ) Notice: Subject to any disclaimer, the term of this patent is extended or adjusted under 35 U.S.C. 154(b) by 739 days.

(21) Appl. No.: 17/071,547

(22) Filed: Oct. 15, 2020

(65) Prior Publication Data
US 2021/0027476 A1    Jan. 28, 2021

Related U.S. Application Data

(63) Continuation of application No. PCT/JP2019/016657, filed on Apr. 18, 2019.

(30) Foreign Application Priority Data

Apr. 18, 2018    (JP) .................................. 2018-080278

(51) Int. Cl.
*G06T 7/33*       (2017.01)
*A61B 3/00*       (2006.01)
(Continued)

(52) U.S. Cl.
CPC ............ *G06T 7/337* (2017.01); *A61B 3/0025* (2013.01); *A61B 3/1241* (2013.01);
(Continued)

(58) Field of Classification Search
CPC ..... A61B 3/0025; A61B 3/1241; A61B 5/163; G06T 7/74; G06T 7/73; G06T 3/0093;
(Continued)

(56) References Cited

U.S. PATENT DOCUMENTS 5,620,000 A    4/1997  Zinser
8,073,205 B2   12/2011 Shinohara
(Continued)

FOREIGN PATENT DOCUMENTS

JP    H04-336677 A    11/1992
JP    H07-146305 A     6/1995
JP    2009-112617 A    5/2009

OTHER PUBLICATIONS

Office Action issued in corresponding Japanese Patent Application No. 2020-514441 dated Apr. 25, 2023 (5 pages).
(Continued)

*Primary Examiner* — Tuan H Nguyen
(74) *Attorney, Agent, or Firm* — FOLEY & LARDNER LLP

(57) ABSTRACT

A first image is projective transformed into a reference image by using a projective transformation matrix on each pixel of the first image. A projective transformation matrix for transforming a tilted image n into a central image G0 is computed based on positions of combinations of twelve corresponding points indicated in a combination of the central image G0 with the tilted image n. The computed projective transformation matrix is then employed to perform a projective transformation of the tilted image n. A projective-transformed tilted image n1 is created thereby.

17 Claims, 11 Drawing Sheets

(51) Int. Cl.
*A61B 3/12* (2006.01)
*G06T 3/00* (2006.01)
*G06T 7/00* (2017.01)
*G06T 7/73* (2017.01)

(52) U.S. Cl.
CPC .......... *G06T 3/0093* (2013.01); *G06T 7/0014* (2013.01); *G06T 7/74* (2017.01); *G06T 2207/20221* (2013.01); *G06T 2207/30041* (2013.01); *G06T 2207/30101* (2013.01)

(58) Field of Classification Search
CPC ......... G06T 7/0014; G06T 7/33; G06T 7/337; G06T 7/00; G06T 3/00; G06T 2207/20221; G06T 2207/30041
See application file for complete search history.

(56) References Cited

U.S. PATENT DOCUMENTS

| | | | |
|---|---|---|---|
| 10,583,068 B2 * | 3/2020 | Du | G02C 7/081 |
| 2011/0279776 A1 * | 11/2011 | Spaide | A61B 3/14 |
| | | | 351/246 |
| 2013/0107210 A1 | 5/2013 | Spaide | |
| 2013/0293843 A1 | 11/2013 | Spaide | |

OTHER PUBLICATIONS

JP Office Action issued in corresponding Japanese Patent Application No. 2020-514441 dated Sep. 26, 2023 (6 pages).

* cited by examiner

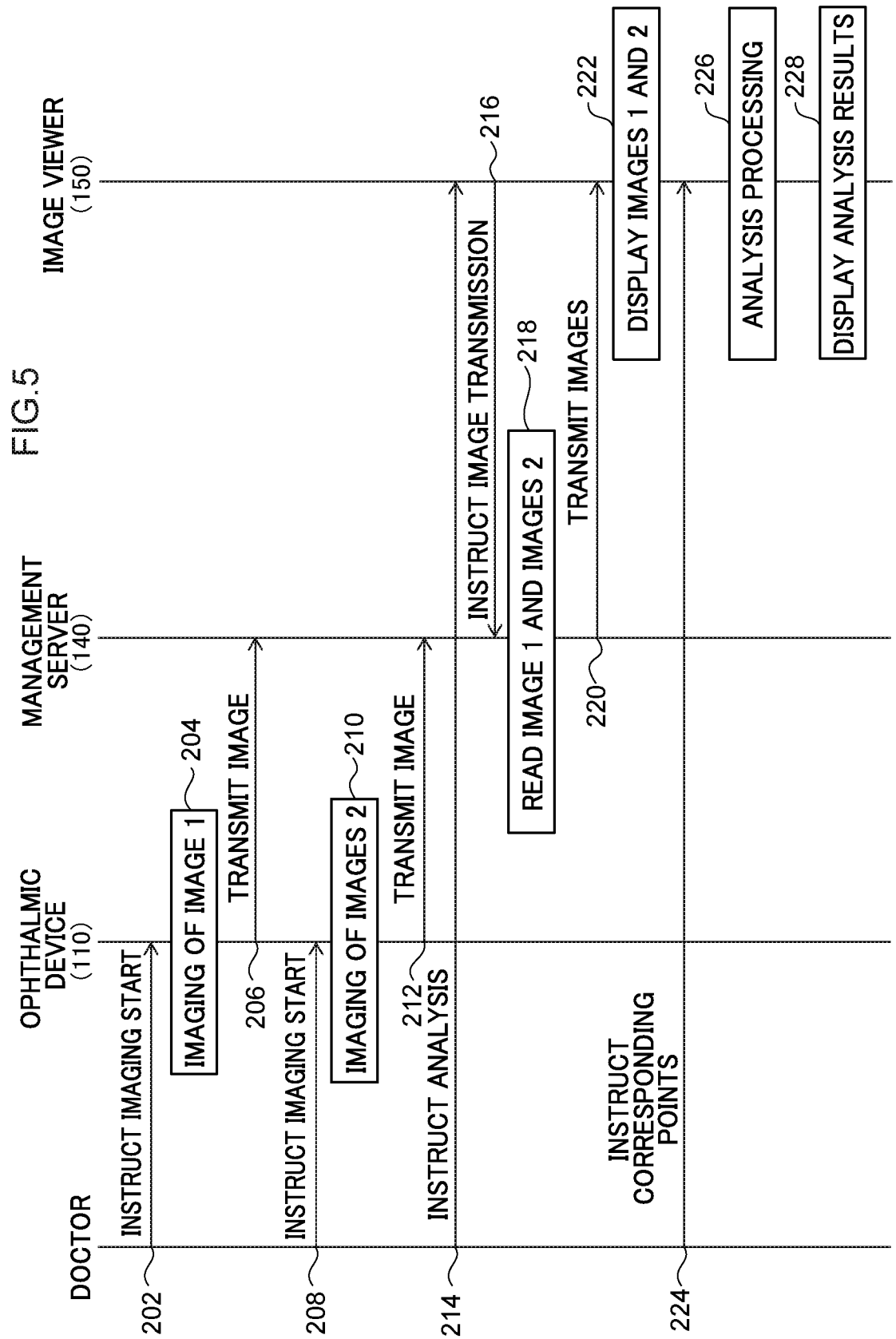

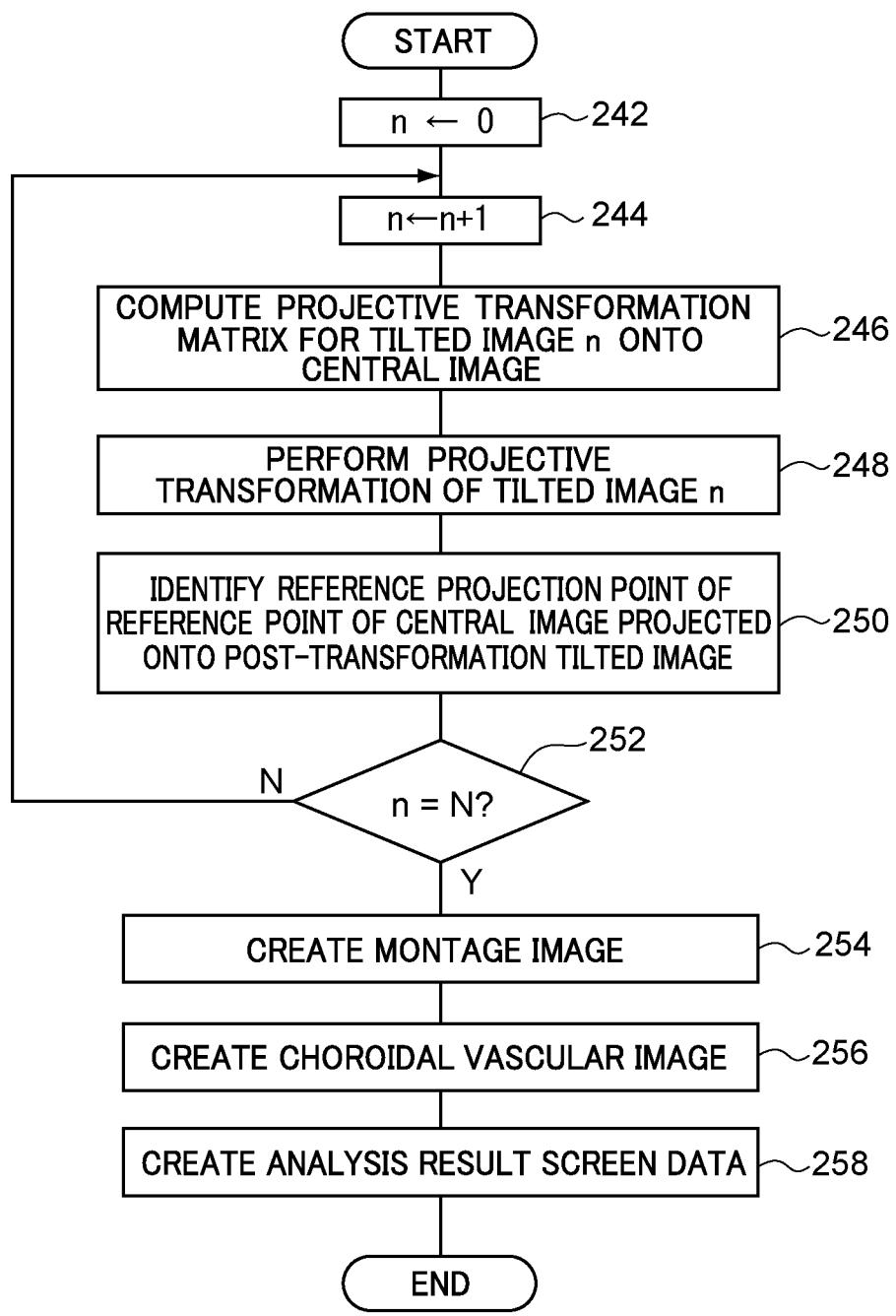

IMAGE PROCESSING METHOD, PROGRAM, AND IMAGE PROCESSING DEVICE

CROSS-REFERENCE TO RELATED APPLICATIONS

This application is a continuation application of International Application No. PCT/JP2019/016657 filed Apr. 18, 2019, the disclosure of which is incorporated herein by reference in its entirety. Further, this application claims priority from Japanese Patent Application No. 2018-080278, filed Apr. 18, 2018, the disclosure of which is incorporated herein by reference in its entirety.

TECHNICAL FIELD

Technology disclosed herein relates to an image processing method, a program, and an image processing device.

RELATED ART

Japanese Patent Application Laid-Open (JP-A) No. 2009-112617 discloses technology relating to a panoramic fundus image synthesizing device and method.

SUMMARY

An image processing method of a first aspect of technology disclosed herein includes: a step of specifying respective corresponding points in a reference image obtained by imaging a fundus with a first gaze and a first image obtained by imaging the fundus with a second gaze different to the first gaze; a step of computing a projective transformation matrix for projective transformation of the first image onto the reference image based on the corresponding points; and a step of employing the projective transformation matrix to perform projective transformation of the first image.

A program of a second aspect of technology disclosed herein causes a computer to execute the image processing method of the first aspect.

An image processing device of a third aspect of technology disclosed herein includes an image processing section configured to execute: a step of specifying respective corresponding points in a reference image obtained by imaging a fundus with a first gaze and a first image obtained by imaging the fundus with a second gaze different to the first gaze; a step of computing a projective transformation matrix for projective transformation of the first image onto the reference image based on the corresponding points; and a step of employing the projective transformation matrix to perform projective transformation of the first image.

BRIEF DESCRIPTION OF DRAWINGS

FIG. 5 is a sequence chart illustrating operations of an ophthalmic system 100.

FIG. 7 is a flowchart illustrating an analysis processing program performed at step 226 in FIG. 5.

DETAILED DESCRIPTION

Detailed explanation follows regarding exemplary embodiments of the present invention, with reference to the drawings. In the following, for ease of explanation, a scanning laser ophthalmoscope is referred to as an "SLO".

Figure 1:
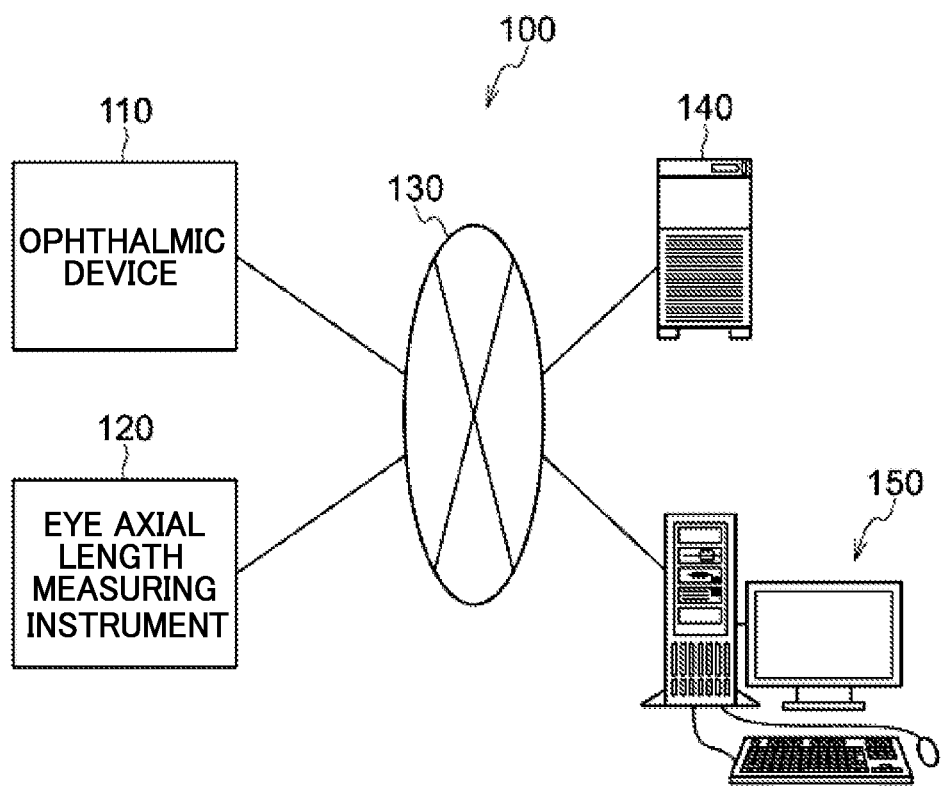
FIG. 1 is a block diagram illustrating an ophthalmic system 100.

The configuration of an ophthalmic system 100 will now be described with reference to FIG. 1. As illustrated in FIG. 1, the ophthalmic system 100 includes an ophthalmic device 110, an eye axial length measuring instrument 120, a management server device (hereinafter referred to as "management server") 140, and an image display device (hereinafter referred to as "image viewer") 150. The ophthalmic device 110 acquires fundus images. The eye axial length measuring instrument 120 measures the eye axial length of a patient. The management server 140 stores plural fundus images and eye axial lengths obtained by imaging the fundi of plural patients using the ophthalmic device 110 in association with respective patient IDs. The image viewer 150 displays fundus images acquired by the management server 140.

The image viewer 150 is an example of an "image processing device" of technology disclosed herein.

The ophthalmic device 110, the eye axial length measuring instrument 120, the management server 140, and the image viewer 150 are connected to each other over a network 130.

Note that other ophthalmic instruments (instruments for tests such as field of view measurement and intraocular pressure measurement) and a diagnostic support device that performs image analysis using artificial intelligence may be connected to the ophthalmic device 110, the eye axial length measuring instrument 120, the management server 140 and the image viewer 150 over the network 130.

Figure 2:
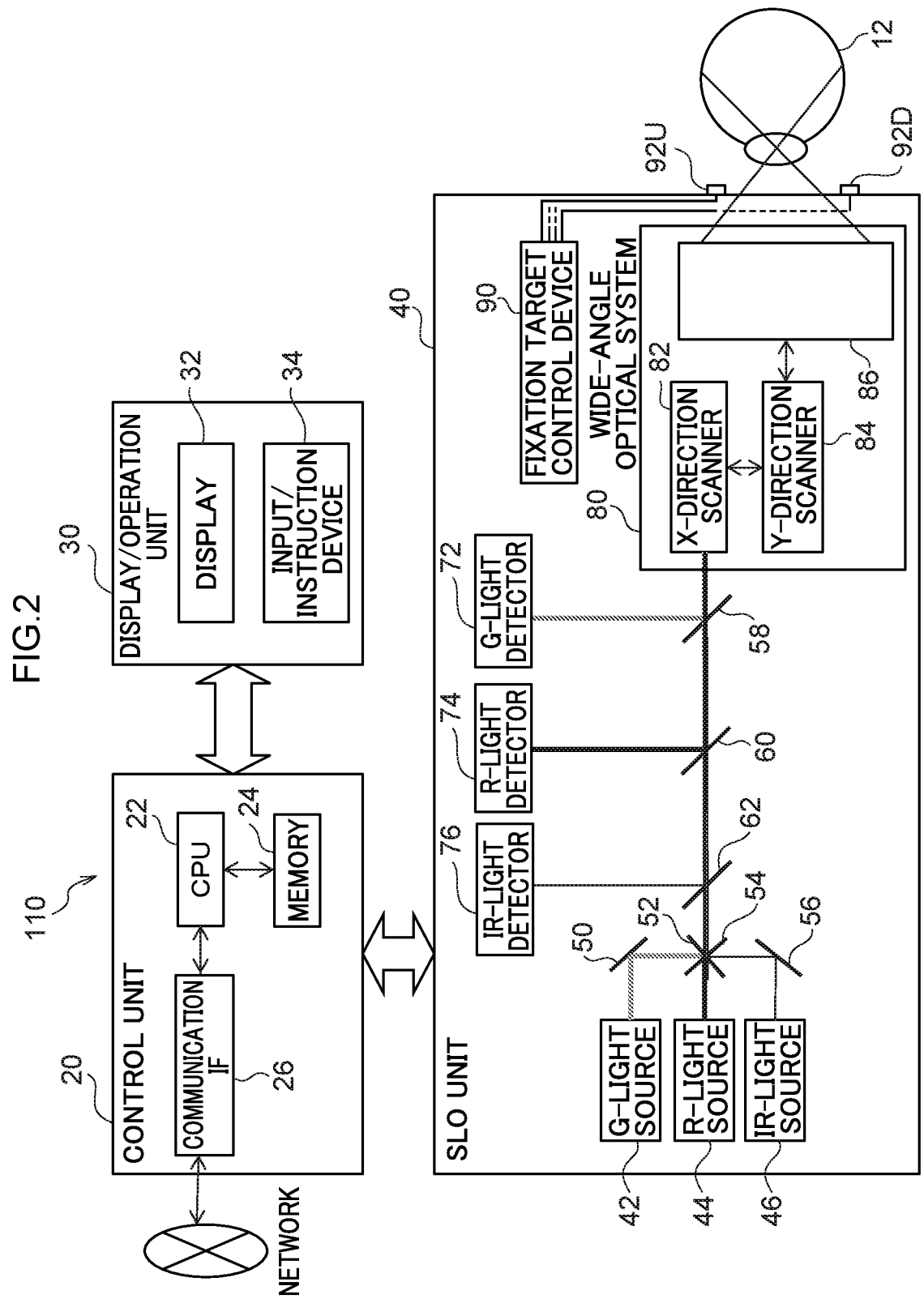
FIG. 2 is a schematic structural view illustrating an overall configuration of an ophthalmic device 110.

Explanation follows regarding a configuration of the ophthalmic device 110, with reference to FIG. 2. As illustrated in FIG. 2, the ophthalmic device 110 includes a control unit 20, a display/operation unit 30, and an SLO unit 40, and images the posterior eye portion (fundus) of the examined eye 12. Furthermore, a non-illustrated OCT unit may be provided for acquiring OCT data of the fundus.

The control unit 20 includes a CPU 22, memory 24, a communication interface (I/F) 26, and the like. The display/operation unit 30 is a graphical user interface that displays an image obtained by imaging and receives various instructions including an imaging instruction. The display/operation unit 30 also includes a display 32 and an input/instruction device 34.

The SLO unit 40 includes a light source 42 for green light (G-light: wavelength 530 nm), a light source 44 for red light (R-light: wavelength 650 nm), and a light source 46 for infrared radiation (IR-light (near-infrared light): wavelength 800 nm). The light sources 42, 44, 46 respectively emit light as commanded by the control unit 20.

The SLO unit 40 includes optical systems 50, 52, 54 and 56 that reflect or transmit light from the light sources 42, 44 and 46 in order to guide the reflected light into a single optical path. The optical systems 50 and 56 are mirrors, and the optical systems 52 and 54 are beam splitters. The G-light is reflected by the optical systems 50 and 54, the R-light is transmitted through the optical systems 52 and 54, and the IR-light is reflected by the optical systems 52 and 56, such that all are guided into a single optical path.

The SLO unit 40 includes a wide-angle optical system 80 for two-dimensionally scanning light from the light sources 42, 44, 46 across the posterior eye portion (fundus) of the examined eye 12. The SLO unit 40 includes a beam splitter 58 that, from out of the light from the posterior eye portion (fundus) of the examined eye 12, reflects the G-light and transmits light other than the G-light. The SLO unit 40 includes a beam splitter 60 that, from out of the light transmitted through the beam splitter 58, reflects the R-light and transmits light other than the R-light. The SLO unit 40 includes a beam splitter 62 that, from out of the light that has passed through the beam splitter 60, reflects IR-light. The SLO unit 40 is provided with a G-light detection element 72 that detects the G-light reflected by the beam splitter 58, an R-light detection element 74 that detects the R-light reflected by the beam splitter 60, and an IR-light detection element 76 that detects IR-light reflected by the beam splitter 62.

The wide-angle optical system 80 includes an X-direction scanning device 82 configured by a polygon mirror to scan the light from the light sources 42, 44, 46 in an X direction, a Y-direction scanning device 84 configured by a galvanometer mirror to scan the light from the light sources 42, 44, 46 in a Y direction, and an optical system 86 including a non-illustrated slit mirror and elliptical mirror to widen the angle over which the light is scanned. The optical system 86 is capable of achieving a field of view (FOV) of the fundus with a larger angle than in conventional technology, enabling a fundus region to be imaged over a wider range than when employing conventional technology. More specifically, a fundus region can be imaged over a wide range of approximately 120 degrees of external light illumination angles from outside the examined eye 12 (in practice approximately 200 degrees about a center O of the eyeball of the examined eye 12 as a reference position for an internal light illumination angle capable of being imaged by illuminating the fundus of the examined eye 12 with scanning light). The optical system 86 may be configured employing plural lens sets instead of a slit mirror and elliptical mirror. Each scanning device of the X-direction scanning device 82 and the Y-direction scanning device 84 may also be scanning devices employing two-dimensional scanners configured by MEMS mirrors.

A system using an elliptical mirror as described in International Applications PCT/JP2014/084619 or PCT/JP2014/084630 may be used in cases in which a system including a slit mirror and an elliptical mirror is used as the optical system 86. The respective disclosures of International Application PCT/JP2014/084619 (International Publication WO2016/103484) filed on Dec. 26, 2014 and International Application PCT/JP2014/084630 (International Publication WO2016/103489) filed on Dec. 26, 2014 are incorporated by reference herein in their entireties.

The ophthalmic device 110 includes fixation targets 92U, 92D, 92L, 92R (see also FIG. 6A to FIG. 6F) that are lit up to attract the gaze of a patient and are configured by light-emitting devices (for example LEDs) provided at positions at the periphery of the optical system 86, offset above, below, and to the left and right of the optical axis thereof. The ophthalmic device 110 further includes a fixation target control device 90 that lights up the fixation targets 92U, 92D, 92L, 92R under the control of the control unit 20.

Note that when the ophthalmic device 110 is installed on a horizontal plane, the "X direction" corresponds to a horizontal direction and the "Y direction" corresponds to a direction perpendicular to the horizontal plane. A direction connecting the center of the pupil of the anterior eye portion of the examined eye 12 and the center of the eyeball is referred to as the "Z direction". The X direction, the Y direction, and the Z direction are accordingly perpendicular to one another.

A color fundus image is obtained by imaging the fundus of the examined eye 12 using G-light and R-light simultaneously. More specifically, the control unit 20 controls the light sources 42, 44 such that the light sources 42, 44 emit light at the same time, and scans the G-light and R-light across the fundus of the examined eye 12 using the wide-angle optical system 80. G-light reflected from the fundus of the examined eye 12 is detected by the G-light detection element 72, and image data of a second fundus image (a green fundus image) is generated by an image processing section 182. Similarly, R-light reflected from the fundus of the examined eye 12 is detected by the R-light detection element 74, and image data of a first fundus image (a red fundus image) is generated by the CPU 22 of the ophthalmic device 110. In cases in which IR-light is illuminated, IR-light reflected from the fundus of the examined eye 12 is detected by the IR-light detection element 76, and image data of an IR fundus image is generated by the CPU 22 of the ophthalmic device 110.

The eye axial length measuring instrument 120 in FIG. 1 has two modes for measuring the eye axial length, this being the length of the examined eye 12 in an eye axial direction, namely a first mode and a second mode. In the first mode, light from a non-illustrated light source is guided into the examined eye 12, and interference light generated from interference between reflected light from the fundus and reflected light from the cornea is received, and the eye axial length is measured based on an interference signal represented by the interference light received. The second mode is a mode in which non-illustrated ultrasound waves are employed to measure the eye axial length. The eye axial length measuring instrument 120 transmits the eye axial length measured using either the first mode or the second mode to the management server 140. The eye axial length may be measured using both the first mode and the second mode, in which case an average of the eye axial lengths measured by the two modes is transmitted to the management server 140 as the eye axial length.

Figure 3:
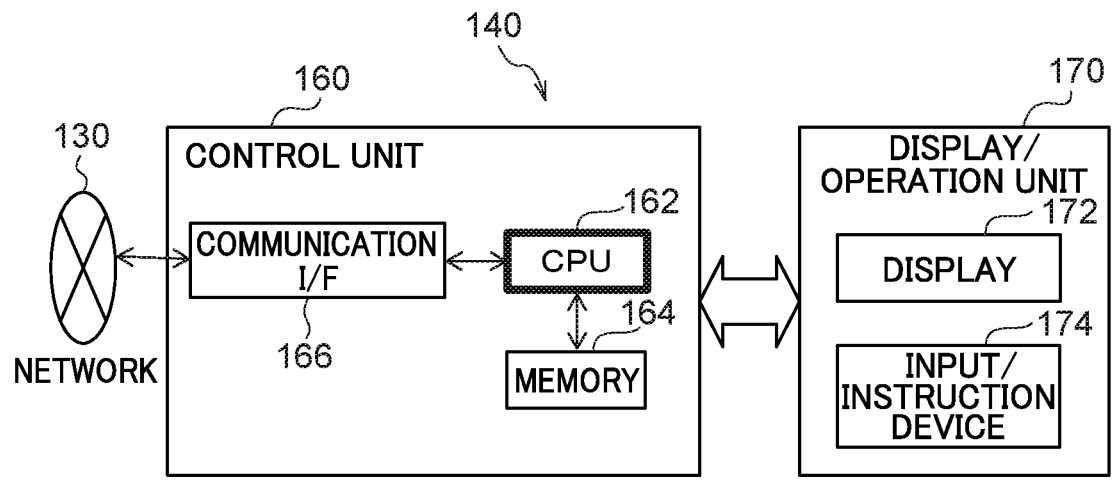
FIG. 3 is a block diagram illustrating a configuration of an electrical system of a management server 140.

Next, explanation follows regarding a configuration of the management server 140, with reference to FIG. 3. As illustrated in FIG. 3, the management server 140 includes a control unit 160, and a display/operation unit 170. The control unit 160 includes a computer including a CPU 162, memory 164 configured by a storage device, a communication interface (I/F) 166, and the like. The display/operation unit 170 is a graphical user interface for displaying images and for receiving various instructions. The display/operation unit 170 includes a display 172 and an input/instruction device 174 such as a touch panel.

Configuration of the image viewer 150 is similar to that of the management server 140, and so explanation thereof is omitted. An analysis processing program is stored in the memory 164 of the image viewer 150.

The analysis processing program is an example of a "program" of technology disclosed herein.

Figure 4:
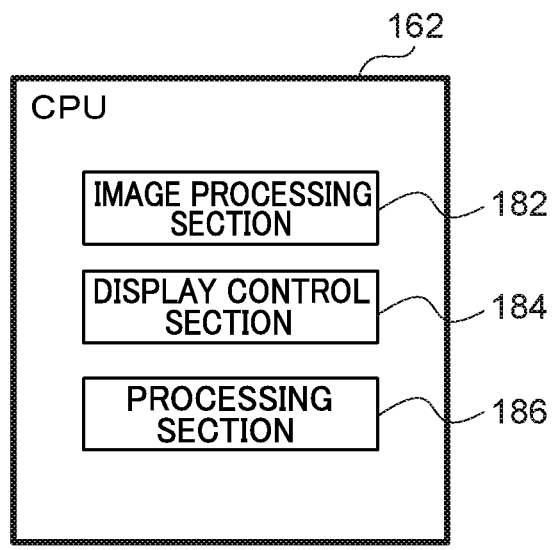
FIG. 4 is a block diagram illustrating functions of a CPU 162 of a management server 140.

Next, with reference to FIG. 4, explanation follows regarding each of various functions implemented by the CPU 162 of the image viewer 150 executing the analysis processing program. The analysis processing program includes an analysis processing function, a display control function, and a processing function. By the CPU 162 executing the analysis processing program including each of these functions, the CPU 162 functions as an image processing section 182, a display control section 184, and a processing section 186, as illustrated in FIG. 4.

Next, explanation follows regarding operation of the ophthalmic system 100, with reference to FIG. 5.

Figure 6A:
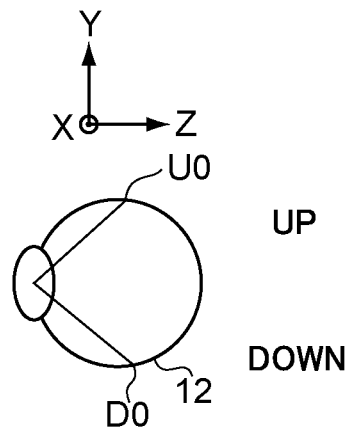
FIG. 6A is a diagram illustrating a fundus imaging range in a plane parallel to an up-down direction passing through pupil and eyeball centers when the optical axis of an examined eye 12 is aligned with an optical axis of an ophthalmic system 100.

The examined eye of the patient is positioned so as to allow imaging of the examined eye of the patient using the ophthalmic device 110. As illustrated in FIG. 5, at step 202 the doctor uses the input/instruction device 34 to instruct the ophthalmic device 110 to start imaging the fundus of the examined eye 12. At step 204, the ophthalmic device 110 images the fundus of the examined eye 12 (an image 1) using the SLO unit 40. The fixation targets 92U, 92D, 92L, 92R are not lit up at step 204. Accordingly, at step 204 the fundus is imaged in a state in which the optical axis of the examined eye 12 is aligned with the optical axis of the ophthalmic system 100, as illustrated in FIG. 6A and FIG. 6D. More specifically, as described above, the fundus of the examined eye 12 is imaged with G light and R light simultaneously to acquire the first fundus image (red fundus image) and the second fundus image (green fundus image), and the image 1 is obtained as a color fundus image from the first fundus image (red fundus image) and the second fundus image (green fundus image). The image 1 acquired by such imaging is, as illustrated in FIG. 6A, a central image G0 (see also FIG. 8) that is imaged over a range from an up position U0 to a down position D0 in the up-down direction as viewed from the ophthalmic system 100, and from a left position L0 to a right position R0 in the left-right direction with respect thereto.

A state in which the optical axis of the examined eye 12 is aligned with the optical axis of the ophthalmic system 100 is an example of a "first gaze" of technology disclosed herein, and the central image G0 is an example of a "reference image" of technology disclosed herein.

When imaging of the image 1 has been completed, at the next step 206 the ophthalmic device 110 transmits the image 1 to the management server 140.

When imaging the image 1 at step 204, various information, such as a patient ID, patient name, age, information as to whether each image is from the right or left eye, the date/time of imaging and visual acuity before treatment, and the date/time of imaging and visual acuity after treatment, is also input to the ophthalmic device 110. The various information described above are transmitted from the ophthalmic device 110 to the management server 140 during image transmission at step 206.

The examined eye of the patient is positioned so as to allow imaging of the examined eye of the patient using the ophthalmic device 110. At step 208, the doctor uses the input/instruction device 34 to instruct the ophthalmic device 110 to start imaging. At step 210 the ophthalmic device 110 performs imaging of images 2. In the processing of step 210, the fundus of the examined eye 12 is imaged as described above with the gaze of the patient looking up, down, left, or right. A left-tilted image (GL (see also FIG. 8)), an up-tilted image (GU), a right-tilted image (GR), and a down-tilted image (GD) are thereby obtained. The left and right directions are as viewed from the ophthalmic device 110. Accordingly, the left-tilted image (GL) is an image obtained by imaging the fundus in a state in which the patient is looking diagonally toward the right, and the right-tilted image (GR) is an image obtained by imaging the fundus in a state in which the patient is looking diagonally toward the left.

Figure 6B:
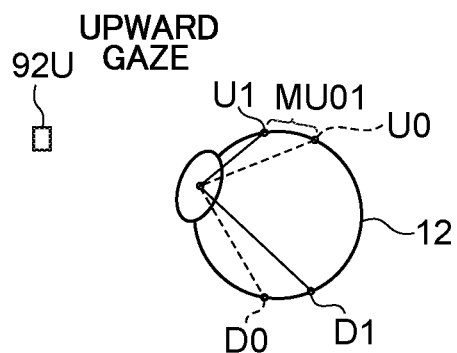
FIG. 6B is a diagram illustrating a fundus imaging range in a plane parallel to an up-down direction passing through pupil and eyeball centers when the optical axis of an examined eye 12 is directed diagonally upward as viewed from an ophthalmic system 100.

For example, in order to direct the gaze of the patient diagonally upward, the fixation target 92U is lit up, such that the gaze of the patient is directed diagonally upward as illustrated in FIG. 6B. The fundus is then imaged in this state. Since the gaze of the patient is directed diagonally upward, imaging is performed as far as an upper side position U1 further to the upper side than the up position U0. An image of a surface MU01 not present in the central image G0 is thus included in the up-tilted image (GU).

Figure 6C:
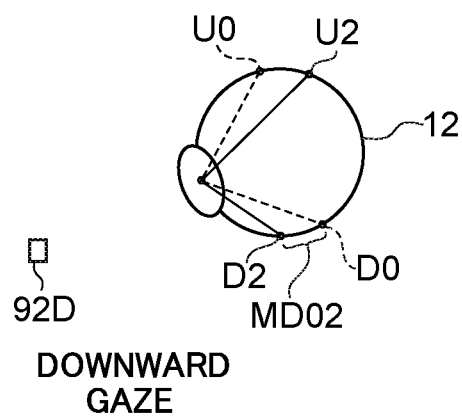
FIG. 6C is a diagram illustrating a fundus imaging range in a plane parallel to an up-down direction passing through pupil and eyeball centers when the optical axis of an examined eye 12 is directed diagonally downward as viewed from an ophthalmic system 100.
Figure 6D:
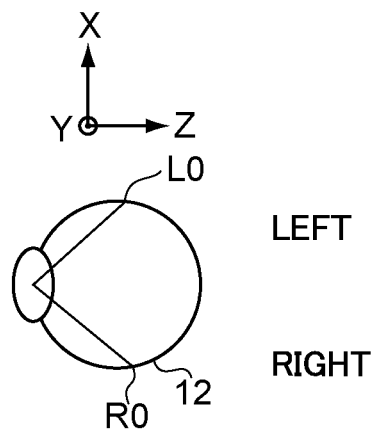
FIG. 6D is a diagram illustrating a fundus imaging range in a plane parallel to a horizontal direction passing through pupil and eyeball centers when the optical axis of an examined eye 12 is aligned with an optical axis of an ophthalmic system 100.

In order to direct the gaze of the patient diagonally downward, the fixation target 92D is lit up, such that the gaze of the patient is directed diagonally downward as illustrated in FIG. 6C. The fundus is then imaged in this state. Since the gaze of the patient is directed diagonally downward, imaging is performed as far as a lower side position D1 further to the lower side than the down position D0. An image of a surface MD02 not present in the central image G0 is thus included in the down-tilted image (GD).

Figure 6E:
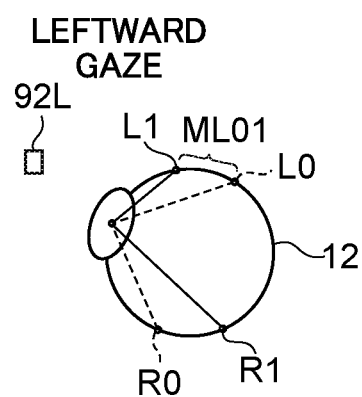
FIG. 6E is a diagram illustrating a fundus imaging range in a plane parallel to a horizontal direction passing through pupil and eyeball centers when the optical axis of an examined eye 12 is directed diagonally toward the left as viewed from an ophthalmic system 100.

In order to direct the gaze of the patient diagonally leftward as viewed from the ophthalmic device 110, the fixation target 92L is lit up. Accordingly, as illustrated in FIG. 6E, the gaze of the patient is directed diagonally leftward (toward the right as viewed from the patient). The fundus is then imaged in this state. Since the gaze of the patient is directed diagonally leftward, imaging is performed as far as a left side position L1 further to the left side than the left position L0. An image of a surface ML01 not present in the central image G0 is thus included in the left-tilted image (GL).

Figure 6F:
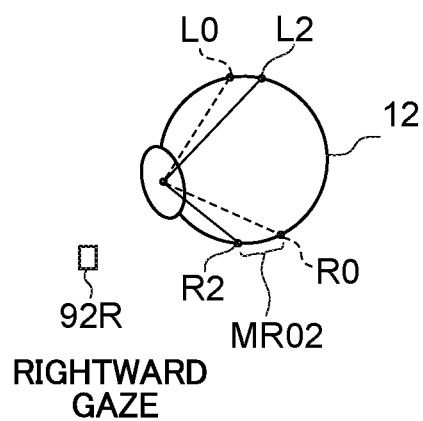
FIG. 6F is a diagram illustrating a fundus imaging range in a plane parallel to a horizontal direction passing through pupil and eyeball centers when the optical axis of an examined eye 12 is directed diagonally toward the right as viewed from an ophthalmic system 100.

In order to direct the gaze of the patient diagonally rightward as viewed from the ophthalmic device 110, the fixation target 92R is lit up. Accordingly, as illustrated in FIG. 6F, the gaze of the patient is directed diagonally rightward (toward the left as viewed from the patient). The fundus is then imaged in this state. Since the gaze of the patient is directed diagonally rightward, imaging is performed as far as a right side position R1 further to the right side than the left position R0. An image of a surface MR02 not present in the central image G0 is thus included in the right-tilted image (GR).

The gazes diagonally upward, downward, leftward, and rightward are examples of a "second gaze" and a "third gaze" of the present disclosure, and the up-tilted image (GU), the down-tilted image (GD), the left-tilted image (GL), and the right-tilted image (GR) are examples of a "first image" and a "second image" of technology disclosed herein.

At step 212, the ophthalmic device 110 transmits the images 2 to the management server 140, including the up-tilted image (GU), the down-tilted image (GD), the left-tilted image (GL), and the right-tilted image (GR).

At step 214, the user (an ophthalmologist or the like) uses the input/instruction device 174 to instruct the image viewer 150 to perform analysis processing.

At step 216, the image viewer 150 instructs the management server 140 to perform image transmission. On being instructed to perform image transmission, at step 218 the management server 140 reads the image 1 and images 2, and at step 220 transmits image data of the image 1 and images 2 to the image viewer 150.

At step 222, the management server 140, to which the image data of the image 1 and images 2 has been transmitted, displays the image 1 and images 2 on the display 172. Specifically, the central image G0 is centrally disposed, and the up-tilted image (GU), the down-tilted image (GD), the left-tilted image (GL), and the right-tilted image (GR) are respectively disposed at the upper side, the lower side, the left side, and the right side of the central image G0.

At step 224, the doctor indicates corresponding points in various combinations of the central image G0 with the up-tilted image (GU), the down-tilted image (GD), the left-tilted image (GL), or the right-tilted image (GR).

For example, the user (an ophthalmologist or the like) looks at the central image G0 and the up-tilted image (GU) displayed on the display 172 and uses the input/instruction device 174 to indicate plural feature points that respectively correspond with each other in the central image G0 and the up-tilted image (GU). The feature points may, for example, be a branch point of blood vessels on the fundus, or the optic nerve head. Moreover, plural points (for example twelve points) are indicated for the feature points. The image viewer 150 receives the plural combinations of feature points (for example twelve pairs thereof) that corresponding across the central image G0 and the up-tilted image (GU). At step 224, the user (ophthalmologist or the like) uses the input/instruction device 174 to indicate plural feature points in each of the combinations of the central image G0 with the down-tilted image (GD), the central image G0 with the left-tilted image (GL), and the central image G0 with the right-tilted image (GR) in a similar manner to as described above. The image viewer 150 receives the combinations plural feature points (for example twelve pairs thereof) for each of the respective combinations.

Indication of the corresponding points at step 224 is not limited to being performed by the user (ophthalmologist or the like), and may be performed automatically based on the image data of the above images. For example, the image processing section 182 may identify corresponding feature points by performing template matching based on the image data for the respective combinations of the central image G0 with the up-tilted image (GU), the down-tilted image (GD), the left-tilted image (GL), or the right-tilted image (GR).

At step 226, the image viewer 150 executes analysis processing, described in detail later, and at step 228 displays an analysis results screen 300 (see FIG. 8) on the display 172. The analysis results screen 300 will be described later.

Next, explanation follows regarding the analysis processing. After the image data of the image 1 and images 2 has been received and displayed (step 222) as described above, when the plural feature point combinations for the respective combinations of images have been received at step 224, the image viewer 150 executes the analysis program at step 266. The analysis processing method illustrated in the flowchart of FIG. 7 is implemented by the CPU 162 of the image viewer 150 executing the analysis processing program. The analysis processing method is an example of an "image processing method" of technology disclosed herein.

At step 242 in FIG. 7, the processing section 186 initializes a variable n for discriminating the tilted images to 0, and at step 244, the processing section 186 increments the variable n by 1. Note that the left-tilted image (GL), the up-tilted image (GU), the right-tilted image (GR), and the down-tilted image (GD) are each respectively discriminated by the variable n=1, 2, 3, or 4. The total number N of instances of the variable n is four.

At step 246, the image processing section 182 computes a projective transformation matrix to transform the tilted image n discriminated by variable n onto the central image G0, based on the positions in the twelve corresponding points combinations specified on combination of the central image G0 with the tilted image n. The projective transformation matrix is a matrix employed for projective transformation so as to transform each pixel in the tilted image n, so that the position of each pixel in the tilted image n is positioned at a corresponding position in the central image G0.

At step 248, the image processing section 182 employs the projective transformation matrix computed at step 248 to perform projective transformation of the tilted image n. A projective-transformed tilted image n1 is created as a result.

At step 250, a reference projection point is identified as a datum point in the central image G0 (for example a center position) projected onto the projective-transformed tilted image n1.

At step 252, the processing section 186 determines whether or not the variable n is the same as the total number N. Cases in which the variable n is not the same as the total number N mean that there is still a tilted image remaining that has not been subjected to the above processing (steps 246 to 250), and so the analysis processing returns to step 244. However, cases in which the variable n is the same as the total number N mean that all of the tilted images have been subjected to the above processing (steps 246 to 250), and so the analysis processing proceeds to step 254.

Through the above processing, different projective transformation matrices are computed to transform each of the left-tilted image (GL), the up-tilted image (GU), the right-tilted image (GR), and the down-tilted image (GD) onto the central image G0. The respective projective transformation matrices are employed on each of the left-tilted image (GL), the up-tilted image (GU), the right-tilted image (GR), and the down-tilted image (GD) to create a post-transformation left-tilted image (GL1), a post-transformation up-tilted image (GU1), a post-transformation right-tilted image (GR1), and a post-transformation down-tilted image (GD1). Reference projection points are then identified as the datum point (for example the center position) of the central image G0 projected onto the post-transformation left-tilted image (GL1), the post-transformation up-tilted image (GU1), post-transformation right-tilted image (GR1), and post-transformation down-tilted image (GD1).

At step 254, the display control section 184 takes the post-transformation left-tilted image (GL1), the post-transformation up-tilted image (GU1), the post-transformation right-tilted image (GR1), and the post-transformation down-tilted image (GD1) and uses these to create an assembled montage image based on the respective reference projection points therein.

Note that the post-transformation left-tilted image (GL1), the post-transformation up-tilted image (GU1), the post-transformation right-tilted image (GR1), and the post-transformation down-tilted image (GD1) each include the first fundus image (red fundus image) and the second fundus image (green fundus image). The montage image accordingly also includes the first fundus image (red fundus image) and the second fundus image (green fundus image).

The structure of the eye is configured by the vitreous body covered by plural layers that each have a different structure. These plural layers include the retina, the choroid, and the sclera from the side closest to the vitreous body outward. R-light passes through the retina and travels as far as the choroid. Accordingly, the first fundus image (red fundus image) includes information relating to blood vessels (retinal blood vessels) present in the retina and information relating to blood vessels (choroidal blood vessels) present in the choroid. By contrast, G-light only travels as far as the retina. Accordingly, the second fundus image (green fundus image) includes information relating to the blood vessels (retinal blood vessels) present in the retina.

At step 256 the display control section 184 creates a choroidal vascular image from the montage image.

The choroidal vascular image is generated in the following manner. The image processing section 182 of the management server 140 subjects the second fundus image (green fundus image) in the montage image to black hat filter processing so as to extract the retinal blood vessels from the second fundus image (green fundus image). Next, the image processing section 182 performs in-painting processing employing the retinal blood vessels extracted from the second fundus image (green fundus image) to remove these retinal blood vessels from the first fundus image (red fundus image) of the montage image. Namely, processing is performed that uses position information relating to the retinal blood vessels extracted from the second fundus image (green fundus image) to infill the retinal blood vessel structures in the first fundus image (red fundus image) with the same pixel values to those of surrounding pixels. The image processing section 182 then subjects the image data of the first fundus image (red fundus image) from which the retinal blood vessels have been removed to contrast-limited adaptive histogram equalization, thereby emphasizing the choroidal blood vessels in the first fundus image (red fundus image). A choroidal vascular image is obtained thereby. The generated choroidal vascular image is stored in the memory 164.

Regarding the method used to generate the choroidal fundus image, the disclosure of Japanese Patent Application No. 2018-052246, filed on Mar. 20, 2018, is incorporated in its entirety by reference herein.

At step 254, the display control section 184 creates analysis result screen data.

Figure 8:
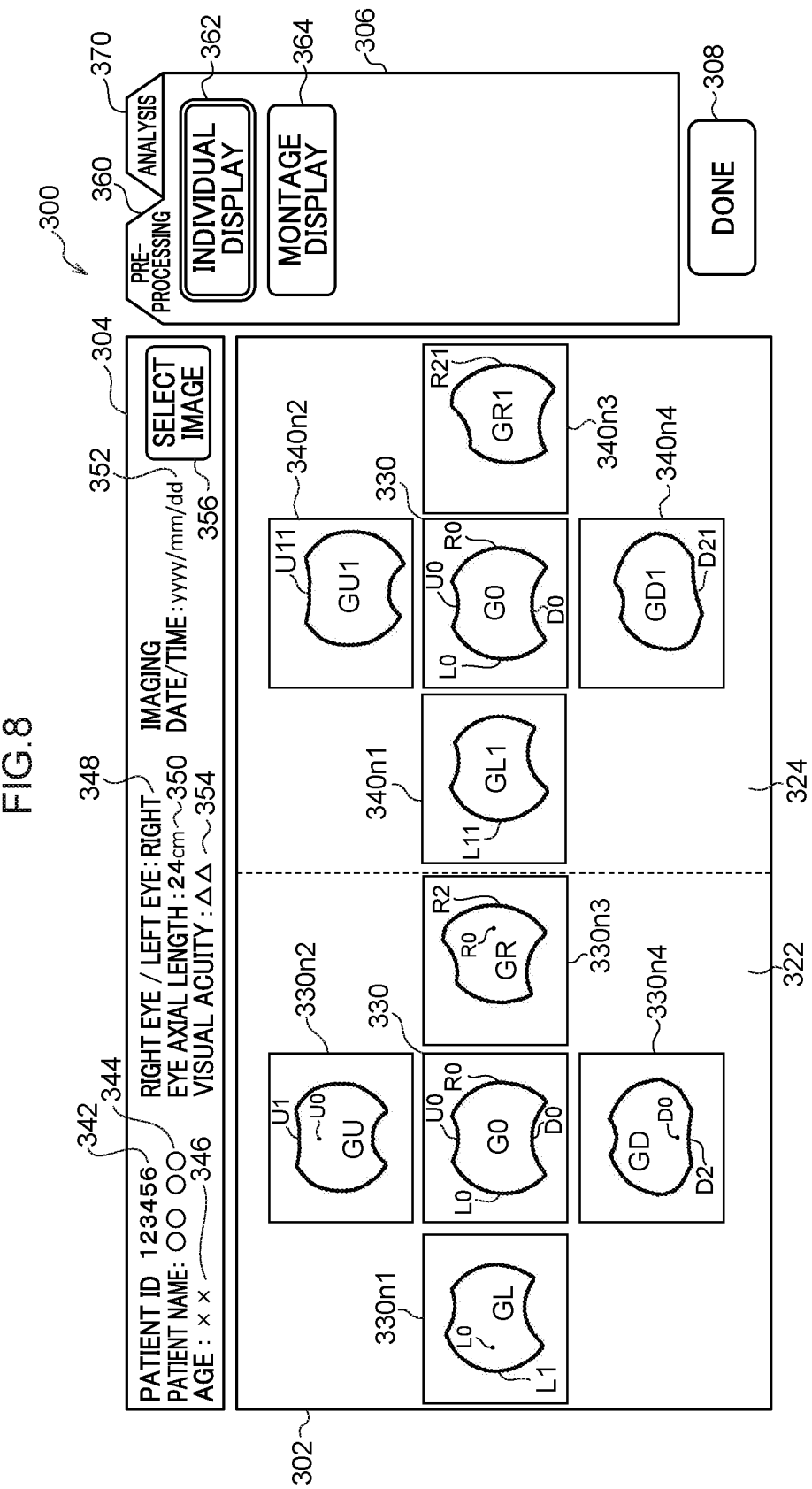
FIG. 8 is a diagram illustrating a display screen for an analysis results screen 300 of an image viewer 150 displayed when an individual display icon 362 in a pre-processing folder 360 has been operated.

FIG. 8 illustrates the analysis results screen 300. As illustrated in FIG. 8, the analysis results screen 300 includes an image display region 302, a patient information display region 304, and a folder display region 306.

A patient ID display region 342, a patient name display region 344, an age display region 346, a display region 348 to display information (right or left) to indicate whether each image is from the left eye or the right eye, an eye axial length display region 350 to display the eye axial length, an imaging date/time display region 352, and a visual acuity display region 354 are provided in the patient information display region 304.

Figure 10:
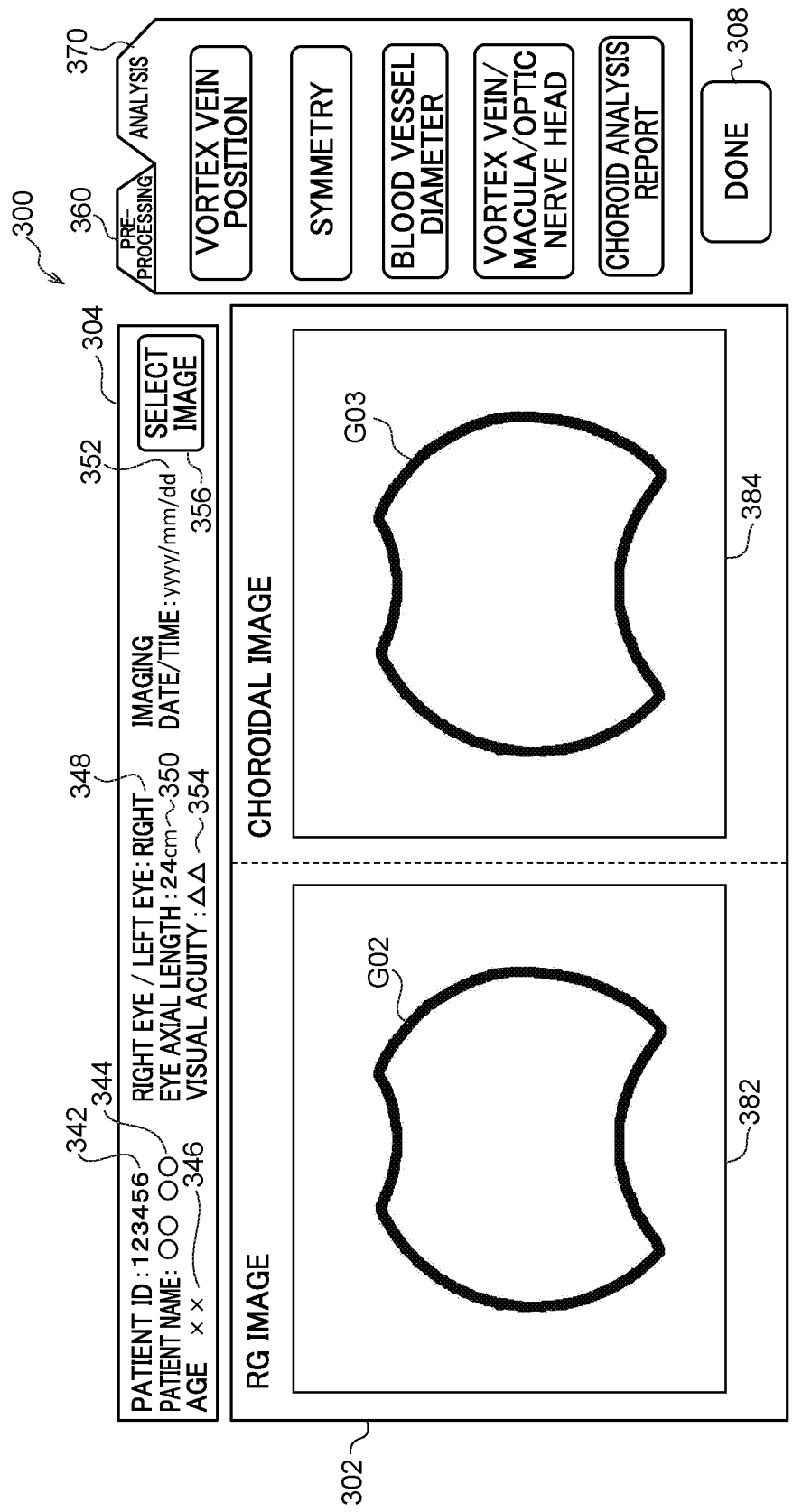
FIG. 10 is a diagram illustrating a display screen for an analysis results screen 300 of an image viewer 150 displayed when an analysis folder 370 has been operated.

The folder display region 306 includes a pre-processing folder 360 and an analysis folder 370. The pre-processing folder 360 is provided with an individual display icon 362 and a montage display icon 3642. Various icons are provided in the analysis folder 370, as illustrated in FIG. 10.

The image display region 302 illustrated in FIG. 8 is displaying content corresponding to a case in which the individual display icon 362 in the pre-processing folder 360 has been operated. As illustrated in FIG. 8, the image display region 302 includes a pre-transformation-image display region 322, and a post-transformation-image display region 324. The pre-transformation-image display region 322 is includes a region 330 to display the central image G0, and regions 330n1 to 330n4 arranged around the region 330 at the center to display the left-tilted image (GL), the up-tilted image (GU), the right-tilted image (GR), and the down-tilted image (GD) at the left side, upper side, right side, and lower side of the region 330, respectively.

The left-tilted image (GL) contains an image extending as far as the left side position L1 further to the left side than the left position L0. The up-tilted image (GU) contains an image extending as far as the upper side position U1 further to the upper side than the up position U0. The right-tilted image (GR) contains an image extending as far as the right side position R1 further to the right side than the left position R0. The down-tilted image (GD) contains an image extending as far as the lower side position D1 further to the lower side than the down position D0.

The post-transformation-image display region 324 includes a region 330 to display the central image G0, and regions 340n1 to 340n4 arranged around the region 330 at the center to display the post-transformation left-tilted image (GL1), the post-transformation up-tilted image (GU1), the post-transformation right-tilted image (GR1), and the post-transformation down-tilted image (GD1) at the left side, upper side, right side, and lower side of the region 330, respectively. The left side position L1 in the left-tilted image (GL) is positioned at a position L11 in the post-transformation left-tilted image (GL1). The upper side position U1 in the up-tilted image (GU1) is positioned at a position U11 in the post-transformation up-tilted image (GU1). The right side position R1 in the right-tilted image (GR1) is positioned at a position R11 in the post-transformation right-tilted image (GR1). The lower side position D1 in the left-tilted image (GD1) is positioned at a position D11 in the post-transformation down-tilted image (GD1).

Icons and buttons for instructing image generation, described later, are displayed on the display screen of the image viewer 150, also described later. When the user of the image viewer 150 (an ophthalmologist or the like) clicks on one of the icons etc., an instruction signal corresponding to the clicked icon etc. is transmitted from the image viewer 150 to the management server 140. On receipt of the instruction signal from the image viewer 150, the management server 140 generates an image corresponding to the instruction signal, and transmits image data of the generated image to the image viewer 150. The image viewer 150 that has received the image data from the management server 140 then displays an image based on the received image data on a display. Display screen generation processing is performed in the management server 140 by the CPU 162 executing a display screen generation program.

Figure 9:
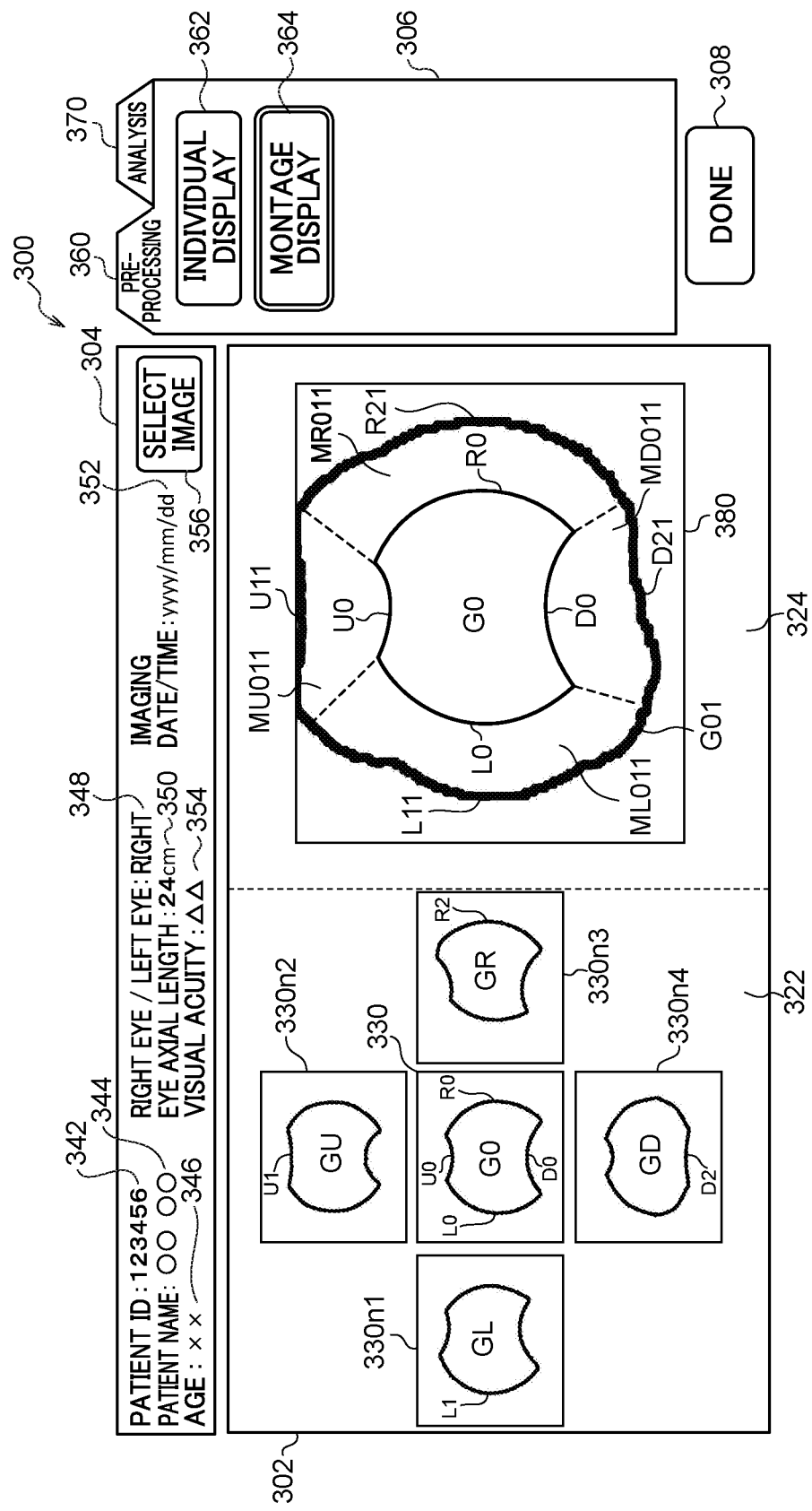
FIG. 9 is a diagram illustrating a display screen for an analysis results screen 300 of an image viewer 150 displayed when a montage display icon 364 in a pre-processing folder 360 has been operated.

When the montage display icon 364 in the pre-processing folder 360 of the analysis results screen 300 illustrated in FIG. 8 is operated, the image display region 302 is changed to the content illustrated in FIG. 9. As illustrated in FIG. 9, the pre-transformation-image display region 322 of the image display region 302 is similar content to that of the region 322 in FIG. 8. On the other hand, the post-transformation-image display region 324 includes a region 380 to display a montage image G01 created at step 254.

The montage image G01 includes the central image G0 and a portion ML011 further to the left side than the central image G0. The portion ML011 is configured by the post-transformation left-tilted image (GL1) from which the central image G0 has been subtracted, and is delineated by lines at the center of respective common portions for portions that are common to the up-tilted image (GU1) and the down-tilted image (GD1), respectively.

The montage image G01 includes a portion MU011 further to the upper side than the central image G0. The portion MU011 is configured by the post-transformation up-tilted image (GU1) from which the central image G0 has been subtracted, and is delineated by lines at the center of respective common portions for portions that are common to the left-tilted image (GL1) and the right-tilted image (GR1), respectively.

The montage image G01 includes a portion MR011 further to the right side than the central image G0. The portion R011 is configured by the post-transformation right-tilted image (GR1) from which the central image G0 has been subtracted, and is delineated by lines at the centers of respective common portions for portions that are common to the up-tilted image (GU1) and the down-tilted image (GD1), respectively.

The montage image G01 includes a portion MD011 further to the lower side than the central image G0. The portion MD011 is configured by the post-transformation down-tilted image (GD1) from which the central image G0 has been subtracted, and is delineated by lines at the centers of respective common portions for portions that are common to the right-tilted image (GR1) and the left-tilted image (GL1).

In this manner, the montage image G01 includes the portion ML011, the portion MU011, the portion MR011, and the portion MD011 arranged around the central image G0. The montage image G01 accordingly includes portions not in the central image G0 obtained by imaging the fundus with the optical axis of the examined eye 12 aligned with the optical axis of the ophthalmic system 100, i.e. the portion ML011, the portion MU011, the portion MR011, and the portion MD011. This enables a greater amount of information to be obtained about the fundus.

FIG. 10 illustrates a display screen displayed in a case in which the analysis folder 370 of the analysis results screen 300 on the image viewer 150 has been operated. As illustrated in FIG. 10, the image display region 302 includes an RG image display region 382 and a choroidal vascular image 384. A montage image G02 is displayed as an RG image in the RG image display region 382. A choroidal vascular image G03 created at step 256 is displayed as the choroidal vascular image 384.

Conventional method technology relating to a panoramic fundus image synthesizing device and method has been disclosed. Such conventional technology does not enable a wider panoramic image to be generated from plural fundus images obtained by imaging the fundus region over a wide range. However, the present exemplary embodiment enables a wider panoramic image (montage image) to be generated from the four fundus images obtained by imaging the fundus while moving the gaze up, down, left, and right.

The conventional technology accordingly does not enable computation of a projective transformation matrix to perform projective transformations on each of the pixels of a first image so that the positions of the respective pixels in the first image are positioned at corresponding positions in a reference image. However, in the present exemplary embodiment, such a projective transformation matrix can be computed, thereby enabling each of the pixels of the first image to be projection transformed using this projective transformation matrix.

Explanation follows regarding various modified examples of the technology disclosed herein.

First Modified Example

Although in the exemplary embodiment described above the wider panoramic image (montage image) is generated from the four fundus images obtained by imaging the fundus while moving the gaze up, down, left, and right, the technology disclosed herein is not limited thereto. For example, a wider panoramic image (montage image) may be generated from four fundus images obtained by imaging the fundus while moving the gaze in other directions such as, for example, diagonally up and to the right, diagonally up and to the left, diagonally down and to the left, and diagonally down and to the right, instead of, or in addition to up, down, left, and right.

Note that the number of fundus images obtained by imaging the fundus while moving the gaze is not limited to four or eight, and is merely one or more.

Second Modified Example

Figure 11:
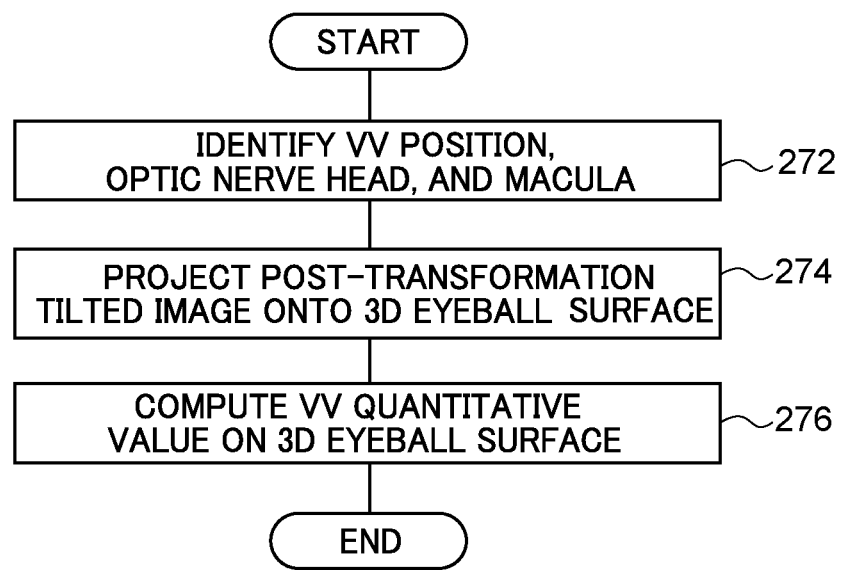
FIG. 11 is a flowchart for a VV quantitative value computation program of a second modified example executed between step 256 and step 258 in FIG. 7.

Although a choroidal vascular image is created in the exemplary embodiment described above (at step 256 in FIG. 7), the technology disclosed herein is not limited thereto. For example, additional processing may be executed between step 256 and step 258 in FIG. 7. FIG. 11 is a flowchart illustrating a VV quantitative value computation program executed between step 256 and step 258 of FIG. 7 in a second modified example.

At step 272 in FIG. 11, the image processing section 182 identifies the position of a vortex vein (hereafter VV) in the choroidal vascular image created at step 256.

The image processing section 182 sets a movement direction (blood vessel running direction) for each choroidal blood vessel appearing in the choroidal vascular image G03 montage image. Specifically, firstly the image processing section 182 executes the following processing for each pixel in the choroidal vascular image G03. Namely, for each pixel the image processing section 182 sets a region (cell) centered on this pixel and creates a histogram of the directions of brightness gradient at each of the pixels in the cell. Next, the image processing section 182 takes the gradient direction having the lowest count in the respective histogram of each cell as the movement direction at the pixel for the cell. The gradient direction corresponds to the blood vessel running direction. Note that the following reason is why the gradient direction having the lowest count corresponds to the blood vessel running direction. Namely, the brightness gradient is small along the blood vessel running direction, whereas the brightness gradient is large along other directions (for example there is a large difference in brightness between blood vessels and tissue other than blood vessels). When the respective histogram of brightness gradients has been created for each of the pixels, then the count in the histogram is small for the direction along the blood vessel running direction. The above processing is performed to set the blood vessel running direction at each pixel in the choroidal vascular image.

The image processing section 182 sets initial positions for M (natural number)×N (natural number) individual elements (=L). Specifically, the image processing section 182 sets M individual positions at uniform spacings in the choroidal vascular image G03 vertically and N individual positions therein horizontally, namely a total of L individual initial positions.

The image processing section 182 then estimates a VV position. Specifically the image processing section 182 performs the following processing at each of the L individual positions. Namely, the image processing section 182 acquires the blood vessel running direction at an initial position (one of the L individual positions), moves this element by a specific distance along the acquired blood vessel running direction, repeats acquisition of the blood vessel running direction but this time at the position moved to, and then moves the element by the specific distance along this acquired blood vessel running direction. Such movements of a specific movement distance along the acquired blood vessel running directions are repeated a preset number of times. The above processing is executed for all of the L individual positions. At this point in time, a point where a given number of elements or more have collected together is taken as the VV position.

At step 272, the image processing section 182 detects the optic nerve head in the green fundus image of the montage image. Specifically, since the optic nerve head is the brightest region in the green fundus image, the image processing section 182 detects as the optic nerve head a region of a specific number of pixels where the pixel values are greatest in the green fundus image that has been read as described above. A center position of the region containing the brightest pixels is computed as the coordinates of the position of the optic nerve head and stored in the memory 164.

Also at step 272, the image processing section 182 detects the macula. Specifically, since the macula is a dark region in the choroidal vascular image, the image processing section 182 detects as the macula a region of a specific number of pixels where the pixel values are smallest in the choroidal vascular image G03 read as described above. The center position of the region containing the darkest pixels is computed as the coordinates of the position of the macula and stored in the memory 164.

Also at step 272, the image processing section 182 identifies positions corresponding to the VV position, the optic nerve head position, and the macula position in the post-transformation left-tilted image (GL1), the post-transformation up-tilted image (GU1), the post-transformation right-tilted image (GR1), and the post-transformation down-tilted image (GD1).

At step 274, the image processing section 182 projects the post-transformation left-tilted image (GL1), the post-transformation up-tilted image (GU1), the post-transformation right-tilted image (GR1), and the post-transformation down-tilted image (GD1) onto a three-dimensional (3D) eyeball surface based on the respective reference projection points.

At step 276, the image processing section 182 computes VV quantitative values from the three-dimensional (3D) eyeball surface having the post-transformation left-tilted image (GL1), the post-transformation up-tilted image (GU1), the post-transformation right-tilted image (GR1), and the post-transformation down-tilted image (GD1) projected thereon.

Computation processing for the VV quantitative values is firstly VV distance computation processing, and is secondly VV angle computation processing.

First, explanation follows regarding the VV distance computation processing. The VV distances are firstly a distance between the optic nerve head position and the VV position, and is secondly a distance between the macula position and the VV position.

Firstly the distance between the optic nerve head position and the VV position, and secondly the distance between the macula position and the VV position, are computed on the three-dimensional (3D) eyeball surface.

Next, explanation follows regarding the VV angle computation processing. VV angles include an angle formed between a line from the macula position to the optic nerve head position and a line from the optic nerve head position to the VV position, and an angle formed between a line from the optic nerve head position to the macula position and a line from the macula position to the VV position. The method of computing the angle θ formed between a line from the macula position to the optic nerve head position and a line from the optic nerve head position to the VV position may employ computation by conformal projection or spherical trigonometry.

The VV quantitative values are included in the analysis result screen data created at step 258 in FIG. 7 in the second modified example. The VV quantitative values are accordingly displayed on the display 172 of the image viewer 150.

Third Modified Example

In the exemplary embodiment described above an example has been described in which a fundus image is acquired by the ophthalmic device 110 with an internal light illumination angle of about 200 degrees. However, the technology disclosed herein is not limited thereto, and the technology disclosed herein may, for example, be applied even when the fundus image imaged by an ophthalmic device has an internal illumination angle of 100 degrees or less.

Fourth Modified Example

In the exemplary embodiment described above the ophthalmic device 110 uses SLO to image the fundus. However, the technology disclosed herein is not limited thereto, and for example the fundus may be imaged using a fundus camera.

Fifth Modified Example

The exemplary embodiment described above describes an example of the ophthalmic system 100 equipped with the ophthalmic device 110, the eye axial length measuring instrument 120, the management server 140, and the image viewer 150; however the technology disclosed herein is not limited thereto. For example, as a first example, the eye axial length measuring instrument 120 may be omitted, and the ophthalmic device 110 may be configured so as to further include the functionality of the eye axial length measuring instrument 120. Moreover, as a second example, the ophthalmic device 110 may be configured so as to further include the functionality of one or both of the management server 140 and the image viewer 150. For example, the management server 140 may be omitted in cases in which the ophthalmic device 110 includes the functionality of the management server 140. In such cases, the analysis processing program is executed by the ophthalmic device 110 or the image viewer 150. Moreover, the image viewer 150 may be omitted in cases in which the ophthalmic device 110 includes the functionality of the image viewer 150. As a third example, the management server 140 may be omitted, and the image viewer 150 may be configured so as to execute the functionality of the management server 140.

Other Modified Examples

The data processing described in the exemplary embodiment described above is merely an example thereof. Obviously, unnecessary steps may be omitted, new steps may be added, and the sequence of processing may be changed within a range not departing from the spirit thereof.

Moreover, although in the exemplary embodiment described above an example has been given of a case in which data processing is implemented by a software configuration utilizing a computer, the technology disclosed herein is not limited thereto. For example, instead of a software configuration utilizing a computer, the data processing may be executed solely by a hardware configuration of FPGAs or ASICs. Alternatively, a portion of processing in the data processing may be executed by a software configuration, and the remaining processing may be executed by a hardware configuration.

What is claimed is:

1. An image processing method comprising:
   specifying respective corresponding points in a reference image obtained by imaging a fundus with a first gaze and in a first image obtained by imaging the fundus with a second gaze which direction is different to direction of the first gaze;
   computing a projective transformation matrix based on the corresponding points;
   employing the projective transformation matrix to perform projection transformation of the first image; and
   synthesizing the reference image together with the projective-transformed first image.

2. The image processing method of claim 1, wherein the projective transformation matrix is a matrix for projective transformation so a position of each pixel in the first image is positioned at a position of a corresponding point in the reference image.

3. The image processing method of claim 1, wherein a reference projection point is identified as a reference point in the reference image projected onto the first image after the projective transformation.

4. The image processing method of claim 1, wherein the corresponding points are a feature point of the fundus present in both the reference image and the first image.

5. The image processing method of claim 1, wherein the corresponding point is a branch point of a blood vessel of the fundus or an optic nerve head.

6. The image processing method of claim 1, further comprising projecting the projective-transformed first image onto a three-dimensional sphere.

7. The image processing method of claim 6, wherein:
   a reference projection point is identified as a reference point in the reference image projected onto the projective-transformed first image; and
   projecting the projective-transformed first image onto a three-dimensional sphere is performed based on the reference projection points.

8. The image processing method of claim 6, further comprising computing a quantitative value according to a plurality of positions on an image projected onto the three-dimensional sphere.

9. The image processing method of claim 8, wherein the quantitative value according to the plurality of positions is computed using spherical trigonometry.

10. The image processing method of claim 8, wherein the quantitative value includes a distance between a vortex vein position and an optic nerve head position or a distance between the vortex vein position and a macula position.

11. The image processing method of claim 8, wherein the quantitative value includes an angle formed between a line from a vortex vein position to an optic nerve head position and a line from the optic nerve head position to a macula position.

12. The image processing method of claim 1, further comprising generating a choroidal vascular image from a synthesized image obtained by the synthesis.

13. The image processing method of claim 12, further comprising identifying a vortex vein position from the choroidal vascular image.

14. The image processing method of claim 1, wherein the reference image and the first image are fundus images imaged using a wide-field fundus imaging device.

15. The image processing method of claim 1, wherein:
   the reference image is a projected image of a posterior pole of the fundus; and
   the first image is a projected image of a portion of the posterior pole and a peripheral portion of the posterior pole.

16. A recording medium recorded with a program to cause a computer to execute an image processing method comprising:
   specifying respective corresponding points in a reference image obtained by imaging a fundus with a first gaze and in a first image obtained by imaging the fundus with a second gaze which direction is different to direction of the first gaze;
   computing a projective transformation matrix based on the corresponding points;
   employing the projective transformation matrix to perform projective transformation of the first image; and
   synthesizing the reference image together with the projective-transformed first image.

17. An image processing device comprising an image processing section configured to execute:
   specifying respective corresponding points in a reference image obtained by imaging a fundus with a first gaze and in a first image obtained by imaging the fundus with a second gaze different to the first gaze;
   computing a projective transformation matrix based on the corresponding points;
   employing the projective transformation matrix to perform projective transformation of the first image; and
   synthesizing the reference image together with the projective-transformed first image.

* * * * *